United States Patent [19]
Callahan et al.

[11] Patent Number: 4,543,349
[45] Date of Patent: Sep. 24, 1985

[54] BASIC HEPTAPEPTIDE VASOPRESSIN ANTAGONISTS

[75] Inventors: James F. Callahan, Philadelphia; Michael L. Moore, Media; Nelson C. Yim, Ambler, all of Pa.

[73] Assignee: SmithKline Beckman Corporation, Philadelphia, Pa.

[21] Appl. No.: 645,127

[22] Filed: Aug. 28, 1984

Related U.S. Application Data

[63] Continuation-in-part of Ser. No. 535,000, Sep. 22, 1983, abandoned.

[51] Int. Cl.$^4$ .................. A61K 37/00; C07C 103/52
[52] U.S. Cl. ...................................... 514/11; 514/807; 260/112.5 R
[58] Field of Search ................. 424/177; 260/112.5 R

[56] References Cited
PUBLICATIONS

M. Manning, et al., Nature, 308 652 & 653 (1984).

Primary Examiner—Delbert R. Phillips
Attorney, Agent, or Firm—William H. Edgerton; Richard D. Foggio; Alan D. Lourie

[57] ABSTRACT

Certain cyclic vasopressin-like peptides, which have an ω-amino- or guanidinoalkyl substituent attached to the cysteine in the 6-position of the ring, have vasopressin antagonist activity. A species of this series of new compounds is [1-(β-mercapto-β,β-cyclopentamethylenepropionic acid)-2-(O-ethyl-D-tyrosine)-4-valine-8-(1,5-diaminopentane)-8-desarginine-9-desglycinamide]-vasopressin.

23 Claims, No Drawings

BASIC HEPTAPEPTIDE VASOPRESSIN ANTAGONISTS

This application is a continuation-in-part of Ser. No. 535,000 filed Sept. 22, 1983, now abandoned.

This invention relates to certain basic cyclic heptapeptides and hexapeptides which are vasopressin antagonists. More specifically, the structures of these cyclic peptides have a 1-($\beta$-mercapto-$\beta,\beta$-cycloalkylene)-propionic acid and five amino acid units cyclized into a 6-unit ring by means of a sulfur derived from the cysteine unit and a sulfur from the propionic acid unit, the ring further having a distinguishing basic amino-alkyl or guanidinoalkyl tail which is attached via an amido linkage to the 6-cysteine unit of the ring, either directly or through another amino acid.

BACKGROUND OF THE INVENTION

M. Manning, W. H. Sawyer and coworkers have published a series of papers describing various [1-($\beta$-mercapto-$\beta,\beta$-cyclopentamethylenepropionic acid), 4-valine]arginine-vasopressin congeners which have anti-vasopressin activity. Among these are Nature, 308 652 (1984), as well as U.S. Pat. Nos. 4,367,225 and 4,399,125.

All of the Manning compounds have a peptide tail attached at unit 6 of the disulfide ring. The present compounds are distinguished over these by being hexapeptides which have a basic tail attached to unit 6 and which also have potent vasopressin antagonist activity.

In the description herein and in the claims, the nomenclature common in the art of peptide and vasopressin chemistry is used. When no configuration is noted, the amino acid unit is in the L, or naturally occurring, form. In certain structural formulas, the thio members of the Cap and Cys units are added for clarity.

Certain of the peptide art designations used herein are the following: Cap, $\beta$-mercapto-$\beta,\beta$-cycloalkylenepropionic acid; Pmp, $\beta$-mercapto-$\beta,\beta$-cyclopentamethylenepropionic acid; Tyr(Alk), O-Alktyrosine; Abu, $\alpha$-amino-n-butyric acid; Cad, cadaverine; Put, putrescine; Put(G), 1-amino-4-guanidinobutane; Chg, cyclohexylglycine; Cha, cyclohexylalanine; Pba, $\alpha$-aminophenylbutyric acid; Gln, glutamic acid amide or glutamine; Gly, glycine; Tyr, tyrosine; Phe, phenylalanine; Phe(4'-Alk), 4'-alkylphenylalanine; N-MeAla, N-methylalanine; Val, valine; Ile, isoleucine; Nle, norleucine; Leu, leucine; Ala, alanine; Lys, lysine; Arg, arginine; Met, methionine; Asn, asparagine; Sar, sarcosine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; Boc, t-butyloxycarbonyl; Z, benzyloxycarbonyl; VSP, vasopressin; HBT, hydroxybenzotriazole; ACM, acetamidomethyl.

"Alk" represents a lower alkyl of 1–4 carbons. For example, these may be optionally attached to the oxygen substituent of a tyrosine unit at position 2 or to the 4'-position of a Phe unit at position 3. Such alkyl substituents include methyl, ethyl, n-propyl, isopropyl or butyl. Ethyl is preferred. When the term, "vasopressin", is used, it means L-arginine vasopressin (AVP) unless otherwise modified. The 1-($\beta$-mercaptocycloalkylene)-propionic acid unit (Cap) at position 1 is often referred herein as Pmp for convenience since the pentamethylene containing unit is preferred.

DESCRIPTION OF THE INVENTION

The basic vasopressin-like compounds of the invention are illustrated by the following structural formula:

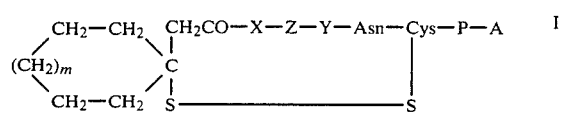

in which:

A is

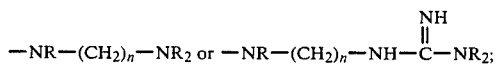

Z is Phe, Phe(4'-Alk) or Tyr(Alk);

X is D-Phe, D-Phe(4'-Alk), D-Val, D-Nva, D-Leu, D-Ile, D-Pba, D-Nle, D-Cha, D-Abu, D-Met, D-Chg, D-Tyr, L-Tyr, D-Tyr(Alk) or L-Tyr(Alk);

P is D-Pro, L-Pro, $\Delta^3$-Pro, L-Ala, N-L-MeAla, Gly, Sar or a single bond;

Y is Val, Ile, Abu, Ala, Chg, Gln, Lys, Cha, Nle, Phe, Leu or Gly;

R is, in each case, hydrogen or $C_{1-5}$-alkyl;

n is an integer from 2–8; and m is an integer from 0–2; or a pharmaceutically acceptable, acid addition salt thereof.

A subgeneric group of compounds of this invention comprises compounds of formula I in which n is 5 and each R is hydrogen which are the cadaverine congeners of this invention.

Also included in this invention are addition salts and complexes of the compounds of this invention, especially the nontoxic, pharmaceutically acceptable salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The end products of formula I have an additional strong basic group in their structures, therefore, their acid addition salt derivatives are easily prepared.

The compounds of formula I are prepared by the following reaction:

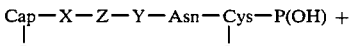

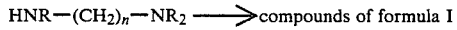

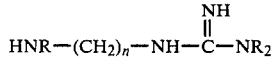

in which X, Z, Y, n, P and R are as defined above for structure I. Cap, of course, refers to the unit at position 1 of the structures of formula I.

The dibasic compound (III) is used in the chemical reaction in a protected form at one of the two basic centers, if necessary. For example, compound whose structure has an amino (—NH₂) or a secondary amino (—NHR), is reacted conveniently as the Boc derivative. When guanidino is present in its structure, reactant III is reacted as a tosylate derivative as known to the art. Other amino protecting groups, which are known to the art, may be used alternatively.

The reaction of the starting material carboxylic acid (II) with the base (III) is carried out using any amide forming reaction common in the peptide art. For example, substantially equimolar quantities of the two starting materials are reacted in the presence of a carbodiimide, such as dicyclohexylcarbodiimide, plus 1-hydroxybenzotriazole in an organic solvent at room temperature until the reaction is complete.

The protective groups are, then, removed by methods known to the art such as reaction in the presence of trifluoromethanesulfonic acid or trifluoroacetic acid/anisole at room temperature for the tosylate (guanidine) or reaction using trifluoroacetic acid in the cold for the Boc (amine) protecting groups.

The guanidino congeners may also be prepared from their amino counterparts directly by reaction of the latter with a compound such as a O-methylisourea. The reaction is usually carried out at a moderately basic pH, in an aqueous solution in the cold, until the reaction is complete.

The starting materials (II) for the reaction described above are part of this invention because they are new compounds which also have VSP antagonist activity, even though at a much higher dose than do the compounds of formula I. These compounds are prepared, as are the end products of formula I, by oxidation of the following linear heptapeptide;

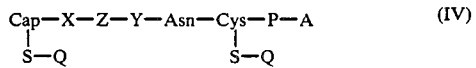

(IV)

in which X, Z, Y, Cap and P are as defined for formula I above and A is OH or as defined for formula I above. The mercapto groups are members of the Cap and Cys units. Each Q is hydrogen or a displaceable group such as acetamidomethyl (ACM). The dithiol of formula IV may be also oxidized in the form of an ester or amide derivative of the unit at position 6 or 7. For example, the amide may be —NHR, —NH₂ or an A-containing amide derivative. The latter, as defined for structure I, gives the end products directly after cyclization, as described in more detail hereafter, and after removal of any protective groups.

Said oxidation is carried out using an excess of an alkali metal ferricyanide, such as potassium or sodium ferricyanide, with the linear intermediate IV. A suitable unreactive solvent, preferably an aqueous-miscible solvent at a neutral pH, about 7–7.5, is used. Reaction is carried out at ambient temperature or lower until the reaction is substantially complete. Preferably, the concentrations of the linear peptide dimercaptan and the oxidizing agent are low, say 0.01–0.1 molar concentration of oxidizing agent in several liters of aqueous solution to cyclize 1–5 grams of dimercaptan.

Other mild oxidation agents having an oxidation potential roughly equivalent to ferricyanide may also be used for the ring closure reaction. Oxygen passage through the reaction solution for several days or iodine in methanol are such alternatives. Cyclization, also, occurs when a displaceable, thiol-protective group such as that at the mercaptan group of the Pmp unit is displaced intramolecularly. An especially useful thio protective group is acetamidomethyl (ACM). Iodine/alcohol is used for direct, one-pot cyclization of the bis-ACM-S-linear peptide. Of course, one skilled in the art will recognize that certain cyclization methods are not appropriate if an interfering reaction site is present in the structure of the starting material of formula IV. The linear mercaptan starting material may have common protective groups temporarily present at the various linear units.

The intermediates of formula IV are conveniently prepared using solid-phase or liquid methods of peptide synthesis.

The peptide chain of the linear peptides is usually built up, stepwise, proceeding from the P unit and working toward the Cap unit. Each unit is properly protected as known in the peptide art and as described below. The sequence of step-reactions is conveniently carried out in a Beckman 990B peptide synthesizer without isolation of each intermediate peptide. The details of the procedure are in the working examples presented hereinafter.

The various amino acids (AA), which are consecutively added to the resin supported chain, are protected as known to the art. For example, the Boc protecting group is used for an amino group, especially at the α-position; an optionally substituted benzyl, for the mercapto groups at the Cap and Cys units; tosyl, for the Arg unit; and an optionally substituted carbobenzoxy(Z) for the Tyr or Lys units. The protective groups should, most conveniently, be those which are easily removed, that is, using acid treatment for the Boc group, sodium-liquid ammonia or catalytic hydrogenation for the benzyl or carbobenzoxy groups.

The resin supported peptide is treated with an excess of anhydrous hydrogen fluoride with an appropriate scavenger compound, such as anisole, to give the linear peptide intermediate of formula IV in good yield.

The end compounds of this invention have vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. We believe the mechanism of action is at the vasopressin receptors (V₂-receptors) located on the plasma membrane of certain renal epithelial cells. The most notable pharmacodynamic effect of the ADH antagonists of the invention is that of a water diuretic rather than of a natriuretic such as hydrochlorothiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease.

The second group of vasopressin receptor sites are the vascular pressor sites (V₁-receptors) within the cardiovascular system itself. These may also be antagonized by the compounds of this invention. The Tyr²-Gln⁴ congeners of formula I are potent V₁-antagonists.

The compounds of this invention, therefore, are used especially to treat edema or to expel water in patients in need of such treatment by administering parenterally or by insufflation a nontoxic but effective quantity of the chosen compound, preferably combined with a pharmaceutical carrier. Dosage units of the active ingredient are selected from the range of 0.05 to 10 mg/kg, preferably 0.1 to 5 mg/kg, of base based on a 70 kg patient. The dosage units are applied from 1 to 5 times daily.

The pharmaceutical composition, which contains an active antagonist ingredient of formula I, comprises a dosage unit which is dissolved or suspended in a standard liquid carrier, such as isotonic saline, and is contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, emulsions or aerosols.

Antagonistic activity toward the natural antidiuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopression binding activity are described by F. Stassen et al., J. Pharmacology and Experimental Therapeutics, 223, 50–54 (1982).

In the test procedure for assay of adenylate cyclase activity, the amount of $^{32}$P/cAMP formed in the absence of medullary membrane is determined (blank). The blank value is subtracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max} = (V_{max}\text{drug}/V_{max} \text{ vasopressin}) \times 100$. $K_i = I/[Ka'/Ka) - 1]$ where I is the concentration of the antagonist, and Ka' and Ka are the concentrations of vasopressin required to give half maximal activity of adenylate cyclase in the presence and absence of antagonist, respectively.

In the test procedure for binding assays, the amount of $^3$H-vasopressin bound in the absence and in the presence of an excess of vasopressin ($7.5 \times 10^{-6}$M) is measured in triplicate. These values represent total and non-specific binding, respectively. The $K_B$ of a compound is derived from the equation for competitive inhibition: $K_B = IC_{50}/(1 + L/K_D)$, where $IC_{50}$ is the concentration required for 50% inhibition of $^3$H-vasopressin ($K_D = 3.6 \times 10^{-9}$M; 1 SD $= 0.4 \times 10^{-9}$M). This is the average $K_D$ value determined on 3 preparations of hog kidney membranes.

The assay for anti-ADH activity in vivo is the hydropenic rat protocol described below:

Hydropenic Rat Screen

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg H$_2$O. A tolerance test is used to determine significance. Ed$_{300}$ is defined as the dose of compound (μg/kg) required to lower urine osmolality to 300 m-Osmoles/kg.

TABLE 1

A [1-(β-Mercapto-β,β-cyclopentamethylenepropionic acid)-2-D-tyrosine-4-valine-8-(1,5-diaminopentane)-8-desarginine-9-desglycineamide]-vasopressin B [1-(β-Mercapto-β,β-cyclopentamethylenepropionic acid)-2-(O—ethyl-D-tyrosine)-4-valine-8-(1,5-diaminopentane)-8-desarginine-9-desglycinamide]-vasopressin C [1-(β-Mercapto-β,β-cyclopentamethylenepropionic acid)-2-(O—ethyl-D-tyrosine)-4-valine-8-(1,4-diaminobutane)-8-desarginine-9-desglycinamide]-vasopressin D [1-(β-Mercapto-β,β-cyclopentamethylenepropionic acid)-2-(O—ethyl-D-tyrosine)-4-valine-8-desarginine-9-desglycinamide]-vasopressin E [1-(β-Mercapto-β,β-cyclopentamethylenepropionic acid)-2-D-tyrosine-4-valine-8-desarginine-9-desglycinamide]-vasopressin F [1-(β-Mercapto-β,β-cyclopentamethylenepropionic acid)-2-(O—ethyl-D-tyrosine)-4-valine-7-desproline-8-desarginine-9-desglycinamide-7-(1,5-diaminopentane)]-vasopressin G [1-(β-Mercapto-β,β-cyclopentamethylenepropionic acid)-2-(O—ethyl-D-tyrosine)-4-valine-8-desarginine-9-desglycinamide-8-(1,4-aminoguanidinobutane)]-vasopressin

| Compound | Rat ED$_{300}$ (μg/kg) | Swine $K_B$ (M) | Swine $K_i$ (M) | Human $K_i$ (M) |
|---|---|---|---|---|
| A | 957 | $2.2 \times 10^{-7}$ | $1.1 \times 10^{-8}$ | — |
| B | 27 | $2.9 \times 10^{-8}$ | $7.2 \times 10^{-9}$ | — |
| C | 19 | $9.2 \times 10^{-9}$ | $6.4 \times 10^{-9}$ | $7.5 \times 10^{-9}$ |
| D | >182 | $4.1 \times 10^{-7}$ | $1.3 \times 10^{-7}$ | — |
| E | >6000 | $1.7 \times 10^{-5}$ | $1.8 \times 10^{-6}$ | — |
| F | 94.5 | $1.9 \times 10^{-8}$ | $6.8 \times 10^{-9}$ | $6.6 \times 10^{-9}$ |
| G | 22 | $1.4 \times 10^{-8}$ | $6.0 \times 10^{-9}$ | $3.5 \times 10^{-9}$ |

The following examples are intended solely to teach the preparation of the compounds of this invention. The temperatures are in degrees Centigrade.

EXAMPLE 1

Procedure for the general synthesis of the cyclic acid intermediates (II):

Boc-Pro-Merrifield resin was made by coupling Boc-Pro to Merrifield resin using the cesium salt method to give Boc-Pro-OCH$_2$C$_6$H$_4$-resin which was used as the starting material for the synthesis. The synthesis was carried out on the Beckman 990 B peptide synthesizer using the following protocol. Three equivalents of the amino acids are dissolved in their appropriate solvents [the Boc derivatives of 4MeBzl-Cys, Val, Phe and 4-MeBzl-Pmp in methylene chloride, Asn in dimethylformamide, X such as D-Tyr(Et) or BrZ-D-Tyr in 1:1 methylene chloride/dimethylformamide] and were coupled using an equimolar amount of dicyclohexylcarbodiimide (DCC) and 1-hydroxybenzotriazole (HBT) except for the coupling of 4MeBzl Pmp where 1.0 equivalent of dimethylaminopyridine was used as catalyst. The extent of coupling was determined by qualitative ninhydrin analyses of each aliquot sample and couplings were repeated when necessary. The Boc groups were removed using 1:1 trifluoroacetic acid/methylene chloride and, after washing, the free amine was generated using 5% diisopropylethylamine/methylene chloride. The sequence of the peptide was checked using solid phase sequencing before the coupling of the 4MeBzl-Pump and its homogeneity confirmed. After the final coupling, the peptide was dried to give 2.24 g of peptide resin in the case of the D-Tyr(Et)$^2$-Pro$^7$-compound.

1.1 Grams (0.5 mmole) of the D-Tyr(Et)$^2$ peptide resin with 3 ml of anisole was stirred 60 min. at 0° (ice bath) in 25 ml of anhydrous liquid hydrogen fluoride (HF). The HF was, then, removed under reduced pressure at 0°. The residue was washed with ethyl ether (4×20 ml, discarded) and the peptide eluted with dimethylformamide (3×10 ml), 20% acetic acid (3×10 ml) and 0.3N ammonium hydroxide (3×10 ml).

The filtrate was added to 2 l of degassed water and the pH adjusted to 7.1 with conc. ammonium hydroxide. A 0.01M solution of potassium ferricyanide was then added dropwise with stirring until a faint yellow color persisted (41 ml).

The resulted solution was then passed through a flash column (5 cm×15 cm) of a packing of silica gel coated with a C-18 silane. The column was, then, washed with 350 ml of water and the peptide eluted with 500 ml of 1:1 acetonitrile/water (0.25% trifluoroacetic acid) in 20 ml fractions.

Fractions 11–17 were combined and concentrated. The residue was dissolved in conc. acetic acid, diluted with water and lyophillized to yield 189 mg of the D-Tyr(Et)$^2$-Pro$^7$ peptide, which was used without further purification for the synthesis of the tail modified peptides.

Identification of:

Amino Acid Analysis: Peptide Content 55%

Asp, 1.00; Pro, 1.23; Cys, 0.35; Val; 1.04, Tyr(Et), 1.43; Phe, 1.51.

HPLC: Satisfactory. (40% CH$_3$CN in H$_2$O with 0.25% TFA).

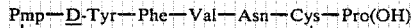

Amino Acid Analysis: Peptide Content 82% Asp, 0.97; Pro, 1.10; Cys, 0.39; Val, 1.05; Tyr, 0.99; Phe, 0.99

HPLC: Satisfactory. (30% CH$_3$CN/70% 0.05 m KH$_2$PO$_4$, 2 ml/min, 5 μC-18, K′=6.14).

EXAMPLE 2

1,5-Diaminopentane (14.0 ml, 120 mmol) was dissolved in tert.-butanol (70 ml) and was treated dropwise over a period of 10 min with di-tert-butyl dicarbonate (9.2 ml, 40 mmol). After the addition had been completed, the reaction mixture was stirred at room temperature for 16.5 hr. The reaction was then treated with 1N sodium hydroxide solution (aq) (90 ml), stirred for 1 hr and finally extracted with chloroform. The chloroform extracts were dried (MgSO$_4$) and concentrated under vacuum. The residue was dissolved in water, made acidic (pH=2) by the dropwise addition of 3N hydrochloric acid at 0° and was washed with ether to remove the diprotected diamine. The aqueous portion was made basic (pH 10) with 5% sodium carbonate solution and was extracted with ethyl acetate to give 1.6 g (20%) of mono-Boc 1,5-diaminopentane. The structure was confirmed by $^1$H NMR and CI-MS.

To a solution of the D-Tyr$^2$-proline heptapeptide, prepared as described in Example 1, (29.7 mg, 0.0331 mmol) and mono-Boc-1,5-diaminopentane (20.2 mg, 0.0996 mmol) in dimethylformamide (400 μl), dicyclohexylcarbodiimide (10.3 mg, 0.05 mmol) and 1-hydroxybenzotriazole hydrate (6.7 mg, 0.05 mmol) were added. The reaction mixture was stirred at room temperature for 19 hours. The dimethylformamide was, then, removed under vacuum. The residue was treated with trifluoroacetic acid at 0° for 2 hours. After this time, the trifluoroacetic acid was removed under vacuum and the residue in 1% acetic acid was passed over a BioRex 70 (H$^+$) ion exchange column. The basic products were washed off the ion exchange column with pyridine buffer (H$_2$O/pyridine/HOAc, 66:30:4) and evaporated. Final purification by prep HPLC (5μ Ultrasphere ODS) gave 5.4 mg (17%) of pure [1-(β-mercapto-β,β-cyclopentamethylenepropionic acid)-2-D-tyrosine-4-valine-8-(1,5-diaminopentane)-8-desarginine-9-desglycinamide]-vasopressin. The structure of the product was confirmed by FAB-MS [(M+H)$^+$=980] and amino acid analysis (Asp=1.00, Pro=1.37, Cys=0.37, Val=0.83, Tyr=0.83, Phe=0.86). The purity was confirmed by HPLC (5μ Ultrasphere ODS, 4.6×250 mm.; 0.05M KH$_2$PO$_4$(-H$_2$O)/CH$_3$CN (70:30); flow=1.5 ml/min; K′=13.7 min.

EXAMPLE 3

Guanidation of monoprotected diamine (III).

Mono-Boc-1,4-diaminobutane (1.25 g, 6.6 mmol), prepared from putrescine as in Example 2, in dioxane (2 ml) and water (6.5 ml) was treated with O-methylisourea hydrogen sulfate (1.25 g, 7.26 mmol) and 2N sodium hydroxide (aq) (3.75 ml) at room temperature. The resulting solution was stirred for 6 days. The solvent was removed under reduced pressure and the residue made basic (pH=12) by the addition of 2N sodium hydroxide. The residue was again evaporated, taken up in ethyl acetate, filtered and evaporated. The crude guanidine was dried by evaporation from toluene and used without further purification.

The crude guanidine (410 mg, 1.78 mmol) in 2N sodium hydroxide (aq) (2 ml) and water (2 ml) was treated at room temperature with p-toluenesulfonyl chloride (340 mg, 1.78 mmol) for 18 hours. The pH was adjusted to 8 with 5% sodium carbonate solution. The mixture was extracted with ethyl acetate to give, upon evaporation, 437 mg of crude product. Purification by flash chromatography (3×15 cm silica bed, 80% ethyl acetate/hexane) gave 265 mg (39%) of the desired tosylated product whose identity was confirmed by $^1$H NMR and CI-mass spectroscopy.

The tosyl-guanidino diamine (108 mg, 0.281 mmol) in methylene chloride (1 ml) was treated with trifluoroacetic acid (1 ml) at 0° for 40 minutes. The reaction was evaporated under vacuum, the residue's pH adjusted to 8 with 5% sodium carbonate solution and evaporated to dryness. The residue was taken up into ethyl acetate, filtered and evaporated. The crude des-Boc product was dried by evaporation from toluene to give 66 mg (82%). Identity was confirmed by $^1$H NMR and used without further purification.

[1-(β-Mercapto-β,β-cyclopentamethylenepropionic acid)-2-D-(O-ethyl)tyrosine-4-valine-8-desarginine-9-desglycinamide]-vasopressin (35 mg, 0.038 mmol), prepared as in Example 1, in dimethylformamide (0.5 ml) was treated at room temperature with the tosyl guanidino amine (33 mg, 0.114 mmol), DCC (12 mg, 0.057 mmol) and HBT (8 mg, 0.057 mmol). The mixture was stirred for 43 hours. The solvent was removed at reduced pressure and the residue was dissolved in trifluoroacetic acid (2 ml), then treated at room temperature with trifluoromethanesulfonic acid (150 μl, 1.7 mmol) and anisole (37 μl) with stirring for 2 hours. The reaction mixture was evaporated to dryness, dissolved in 10% acetic acid, filtered and passed through a BioRex ®-70 column. The crude guanidine was eluted off the column with pyridine buffer (pyridine/water/acetic acid, 30:66:4), evaporated and the residue purified by preparative HPLC (5μ, ODS, CH$_3$CN/H$_2$O/TFA 40:60, 0.25%) to give 6.9 mg of 85% pure [1-(β-mercapto-β,β-cyclopentamethylenepropionic acid)-2-D-(O-ethyl)-tyrosine-4-valine-8-(1-amino-4-guanidinobutane)-8-desarginine-9-desglycinamide]-vasopressin. Preparative HPLC of half of this crude sample, first using 60% 0.05M KH$_2$PO$_4$ (aq):40% CH$_3$CN, then using 60% H$_2$O:40% CH$_3$CN:0.25% TFA gave 1 mg of product which was homogeneous by HPLC and TLC and whose structure was confirmed by FAB-MS [(M+H)$^+$=1036, (M−H)$^-$=1034]. HPLC: (60% 0.05m KH$_2$PO$_4$:40% CH$_3$CN), IBM 5μ C-18, 4.6×250 mm, Flow 1.5 ml/min K'=14.2 min.

EXAMPLE 4

A solution of 40 mg (0.043 mmol) of the D-Tyr(Et)$^2$-proline, prepared as in Example 1, and mono-Boc-1,5-diaminopentane (26 mg, 0.129 mmol) in dimethylformamide (900 μl) was treated with dicyclohexlcarbodiimide (13 mg, 0.065 mmol) and 1-hydroxybenzotriazole hydrate (9 mg, 0.065 mmol) with stirring at room temperature for 43 hours. The dimethylformamide was, then, removed under vacuum. The residue was treated with trifluoroacetic acid at 0° for 1 hour. After this time, the trifluoroacetic acid was removed under vacuum and the residue in 1% acetic acid was passed through a BioRex 70 (H+) ion exchange column. The basic products were washed off the column with pyridine buffer (H$_2$O/pyridine/acetic acid, 66:30:4) and evaporated. Final purification by prep HPLC (5μ Ultrasphere ODS) gave 13 mg (30%) of pure [1-(β-mercapto-β,β-cyclopentamethylenepropionic acid)-2-(O-ethyl-D-tyrosine)-4-valine-8-(1,5-diaminopentane)-8-desarginine-9-desglycinamide]-vasopressin. The structure of the product was confirmed by FAB-MS [(M+H)$^+$=1008] and its purity confirmed by HPLC (5μ Ultrasphere ODS, 4.6×250 mm, 60% H$_2$O, 40% CH$_3$CN (0.25% TFA added), K'=17.9 mins.)

EXAMPLE 5

A solution of 1,4-diaminobutane (10 ml, 99.5 mmol) in methylene chloride (70 ml) was treated with di-tert-butyl dicarbonate (7.24 g, 33.2 mmol) at 0° and the resulting solution stirred at room temperature for 71 hours. The reaction mixture was diluted with chloroform (75 ml), washed with 5% sodium carbonate (aq), dried (MgSO$_4$) and evaporated. The crude residue was dissolved in a minimum of 1N hydrochloric acid (aq) (10 ml) and washed with water (2×). The aqueous fraction was made basic (pH=10) with 2N sodium hydroxide (aq) and extracted with ethyl acetate. The extract was dried (MgSO$_4$) and evaporated to give 821 mg (13%) pure t-Boc-putrescine (1,4-diaminobutane) whose structure was confirmed by 'H NMR and CI-MS [(M+H)$^+$=189].

A solution of 48.6 mg (0.0526 mmol) of the D-Tyr-(Et)$^2$-proline, prepared as in Example 1, and mono-t-Boc 1,4-diaminobutane (30 mg, 0.158 mmol) in dimethylformamide (500 μl) was treated with dicyclohexylcarbodiimide (16 mg, 0.079 mmol) and 1-hydroxybenzotriazole hydrate (11 mg, 0.079 mmol), then stirred at room temperature for 114 hours. The dimethylformamide was removed under vacuum. The residue was treated with trifluoroacetic acid at 0° for 2 hours. The trifluoroacetic acid was removed under vacuum and the residue in 1% acetic acid was passed through a BioRex 70 (H+) ion exchange column. The basic products were washed off the ion exchange column with pyridine buffer (H$_2$O/pyridine/acetic acid, 66:30:4) and evaporated to give [1-(β-mercapto-β,β-cyclopentamethylenepropionic acid)-2-(O-ethyl-D-tyrosine)-4-valine-8-(1,4-diaminobutane)-8-desarginine-9-desglycinamide]-vasopressin. Final purification by prep HPLC (5μ Ultrasphere ODS) gave 19 mg (36%) pure product. The structure of the product was confirmed by FAB-MS [(M+H)$^+$=994, (M-H)$^-$=992] and amino acid analysis (Asp=1.00, Pro=0.98, Cys=0.73, Val=0.94, Tyr=0.86, Phe=0.94). The purity was confirmed by HPLC (5μ Ultrasphere ODS, 4.6×250; 60:40, 0.05 MKH$_2$PO$_4$:CH$_3$CN, k'=11.2 min; gradient 80:20 to 60:40, 0.05 MKH$_2$PO$_4$:CH$_3$CN; k'=41.3 min).

Substituting O-methyl-L-tyrosine in the chemical procedure above gives [1-(β-mercapto-β,β-cyclopentamethylenepropionic acid)-2-(O-methyl-L-tyrosine)-4-valine-8-(1,4-diaminobutane)-8-desarginine-9-desglycinamide]vasopressin. Using similarly protected β-(S-benzylmercapto-β,β-cyclotetramethylene)-propionic acid in place of Pmp in the method of Examples 1 and 2 gives [1-(β-mercapto-β,β-cyclotetramethylene-propionic acid)-2-D-tyrosine-4-valine-8-(1,5-diaminopentane)-8-desarginine-9-desglycinamide]-vasopressin. Substituting dimethylaminoethylamine for Boc-putrescine in Example 4 gives [1-(β-mercapto-β,β-cyclopenta-methylenepropionic acid)-2-(O-ethyl-D-tyrosine)-4-valine-8-(2-dimethylaminoethane)-8-desarginine-9-desglycinamide]-vasopressin. Substituting monoformylcadaverine above followed by reduction of the formyl group gives the N-methylcadaverine derivative.

EXAMPLE 6

O-Methylisourea hydrogen sulfate (88 mg, 0.511 mmol) was dissolved in water (3 ml) and the pH adjusted to 10 using 3N NaOH(aq). Then, [1-(β-mercapto-β,β-cyclopentamethylenepropionic acid)-2-D-(O-ethyl)tyrosine-4-valine-8-8-desarginine-9-desglycinamide-8-(1,4-diaminobutane]vasopressin from above (8.3 mg, 0.00835 mmol) was added in water (2 ml). The pH was corrected to 10 and the solution was kept in the refrigerator for 17 days. The pH of the solution was adjusted to 4.5 with 1% HOAc(aq). The solution was stripped, taken up in 1:1 H$_2$O:CH$_3$CN and purified by preparation HPLC (5μ ODS) to give 5.5 mg (64%) of [1-(β-mercapto-β,β-cyclopentamethylenepropionic acid)-2-(O-ethyl-D-tyrosine)-4-valine-8-(1-amino-4-guanidinobutane)-8-desarginine-9-desglycinamide]-vasopressin. The structure was confirmed by FAB-MS [(M+H=1036]. The purity was confirmed by HPLC (5μ ODS, IBM, 4.6×250 mm; 60:40, 0.05M KH$_2$PO$_4$:CH$_3$CH, k'=17.2 min; gradient 80:20 to 50:50, 0.05M KH$_2$PO4: CH$_3$CN, K'=32.3 min.

EXAMPLE 7

Synthesis of Pmp—D-Tyr(Et)—Phe—Val—Asn—Cys(OH):

The titled compound was prepared by means of solid phase as described in Example 1 but using Boc-Cys-Merrifield resin as starting material which was subsequently coupled with the appropriate Boc-amino acid sequentially, followed by hydrogen fluoride deprotection, cleavage from the resin concurrently and, then, oxidative cyclization were carried out as described. Purification:
(1) $C_{18}$ flash column chromatograph
(2) Preparative HPLC Yield: 65 mg from 0.5 mmoles (molecular weight 827) $65/827 \times 100\% = 16\%$ A.A. cont: 85% based on N analysis FAB MS: 827 positive observed 825 negative observed A.A. analysis: Asp 1; Tyr 0.98; Cys 0.47; Phe 0.94; Val 0.96.

HPLC analysis: One peak using 40% $CH_2CN$ an 0.1% aqueous TFA solution with $5\mu$ $C_{18}$ column

EXAMPLE 8

A solution of 32.6 mg (0.0394 mmol) of the D-Tyr-(Et)-cysteine acid, prepared as in Example 7, and mono-t-Boc-1,5-diaminopentane (24 mg, 0.118 mmol) in dimethylformamide (1 ml) was treated with dicyclohexylcarbodiimide (12 mg, 0.059 mmol) and 1-hydroxybenzotriazole hydrate (8 mg, 0.059 mmol) and was stirred at room temperature for 90 hours. The dimethylformamide was then removed under vacuum. The residue was treated with trifluoroacetic acid (5 ml) at 0° for 3 hours. After this time, the trifluoroacetic acid was removed under vacuum and the residue therefrom dissolved in 10% acetic acid, then passed through a BioRex 70 (H+) ion exchange column. The basic products were washed off the ion exchange column with pyridine buffer (water/pyridine/acetic acid, 66:30:4) and evaporated to dryness to give [1-($\beta$-mercapto-$\beta$,$\beta$-cyclopentamethylenepropionic acid), 2-(O-ethyl-D-tyrosine)-4-valine, 7-(1,5-diaminopentane), 7-desproline, 8-desarginine, 9-desglycinamide]-vasopressin. Final purification by preparative HPLC (using $5\mu$ Ultrasphere ODS) (2 times) gave 4.7 mg (13%) pure product. The structure of the product was confirmed by FAB-MS [(M+H)+ =911] and amino acid analysis (Asp=1.00, Cys=0.46, Val=1.01, Tyr=0.90, Phe=0.99). The purity was confirmed by HPLC ($5\mu$ Ultrasphere ODS, 4.6×250 mm, 60:40, 0.05M $KH_2PO_4/CH_3CN$, $K^1 = 16.7$ min, gradient 80:20 to 50:50, 0.05M $KH_2PO_4/CH_3CN$, $K^1 = 32.3$ min).

EXAMPLE 9

Diaminoheptane (13.0 g, 100 mmol) was dissolved in 100 ml of methylene chloride. To this was added 8.72 g of di-t-butyldicarbonate (40 mmol) in 10 ml of methylene chloride over one hour. After stirring at room temperature overnight, a white precipitate formed which was collected by filtration. It was dissolved in 1N ammonium hydroxide and extracted with ethyl acetate. The ethyl acetate was washed with water and evaporated to dryness. The residue was dissolved in 1N sodium bisulfate, extracted with ethyl acetate and then made basic (pH 8–9) with ammonium hydroxide. This solution was extracted with ethyl acetate. The ethyl acetate was dried over magnesium sulfate and evaporated to dryness, yielding a pale yellow oil which solidified upon standing. The solid was triturated with hexane, collected by filtration and air-dried, yielding 350 mg (2%), mp 55–58, FAB-MS and proton NMR consistent with the structure of Boc-diaminoheptane.

Twenty-five milligrams of the Pro-OH peptide of Example 1 (27 $\mu$mol) was dissolved in 5 ml of dimethyl formamide. To this was added 31 mg Boc-diaminoheptane (135 $\mu$mol, 5 eq), 18.3 mg of HBT (135 umol) and 21 $\mu$l of di-isopropylcarbodiimide (135 $\mu$mol). After stirring at room temperature overnight, the solvent was removed under vacuum. The residue was dissolved in chloroform which solution was washed with 1N sodium bisulfate followed by saturated brine and, then, evaporated to dryness several times from chloroform. The residue was dissolved in 4N HCl/dioxane and stirred at room temperature for 30 minutes. After evaporation of solvent, the residue was evaporated several times from chloroform, dissolved in water, adjusted to pH 3.5 with glacial acetic acid and applied to a BioRex 70 column (H+). The column was washed with water and then eluted with pyridine acetate buffer (30% pyridine, 6% acetic acid). The buffer was evaporated to dryness and the residue lyophilized out of water. The peptide, [1-($\beta$-mercapto-$\beta$,$\beta$-cyclopentamethylenepropionic acid)-2-(O-ethyl-D-tyrosine)-4-valine-8-desarginine-9-desglycinamide-8-(1,7-diaminoheptane)]-vasopressin, was purified by gel filtration chromatography on P-2 in 1% acetic acid followed by preparative HPLC.

EXAMPLE 10

Procedure for solid phase synthesis of cyclic hexapeptides of formula II:

Boc-S-acetamidomethyl-L-cysteine is attached to chloromethylated polystyrene via the cesium salt method as described previously. Removal of Boc is accomplished with 50% TFA/methylene chloride, neutralization with 10% triethylamine/methylene chloride. Coupling is accomplished with dicyclohexylcarbodiimide/hydroxybenzotriazole (or DCC/dimethylaminopyridine (DMAP) in the case of the Pmp residue) according to the standard solid phase protocol. Boc-L-asparagine is coupled in DMF. Boc-L-valine, Boc-L-phenyl-alanine, Boc-O-ethyl-D-tyrosine and S-acetamidomethylpentamethylenemercaptopropionic acid are then sequentially coupled in methylene chloride. The linear peptide (IV) is cleaved from the resin with anhydrous liquid HF at 0° and the resin is washed with ethyl ether and, then, extracted with 50% aqueous acetonitrile/1% TFA, DMF, and 0.3N ammonium hydroxide. The combined extracts are evaporated to dryness. The residue is dissolved in methanol and treated with an excess of methanolic iodine at room temperature to effect deprotection of the sulfhydryls and oxidation to the disulfide. After evaporation of the solvent, the residue is dissolved in 0.3N ammonium hydroxide, diluted with water and lyophilized to yield the crude cyclohexapeptide of Example 7 which is purified by countercurrent distribution followed by gel filtration.

EXAMPLE 11

Procedure for solid phase synthesis of the basic end products of formula I:

Boc-S-(p-methylbenzyl)-L-cysteine is condensed with carbobenzoxycadaverine in methylene chloride using DCC/HOBT. The Boc is removed with 4N HCl/dioxane and the HCl salt is neutralized with triethylamine. The S-(p-methylbenzyl)-L-cysteinyl-carbobenzoxycadaverine is, then, condensed with fluorenylmethyloxycarbonyl-beta-t-butyl-L-aspartic acid in DMF using DCC/HBT. The t-butyl ester is removed with 50% TFA/methylene chloride and the resulting Fmoc-Asp-Cys(MeBzl)-Cad-Z is coupled to benzhydrylamine resin using DCC/DMAP. After removal of the Fmoc group with piperidine, the peptide is elongated according to the standard solid phase procedure as in Example 1. Treatment of the peptidyl resin with anhydrous liquid HF at 0 degrees affords the completely deprotected 7-(1,5-diaminopentane)hexapeptide (IV), which is then oxidized to the cyclic disulfide end product with potassium ferricyanide in dilute aqueous solution as exemplified previously.

EXAMPLE 12

Procedure for solution synthesis of basic end products of formula I:

One equivalent of mono-carboxybenzyl diamine (n=2-8) is coupled to one equivalent Boc-proline in methylene chloride using 1.0 equivalent of 1-hydroxybenzotriazole hydrate and 1.1 equivalents dicyclohexylcarbodiimide at room temperature for 18 hours. The reaction mixture is filtered and evaporated. The crude product is purified by flash chromatography (silica gel) to give pure Boc-Pro-A.

The Boc protecting group is removed from the bis unit compound by using 4N HCl in dioxane at room temperature for 1.5 hours followed by evaporation of the reaction mixture to dryness. The hydrochloride salt is, then, converted to the free amine using triethylamine (1 equivalent) in methylene chloride or dimethylformamide depending upon solubility. The peptide is elongated by successive couplings with Boc-cysteine (S-Acm), Boc-asparagine, and Boc-valine to give the tetrapeptide, Boc-Val-Asn-Cys(S-Acm)-Pro-A. After removal of the Boc group, this tetrapeptide is condensed with Pmp(S-Acm)-D-Tyr(Et)-Phe-OH, prepared by successive couplings of Boc D-Tyr(Et) and Pmp(S-Acm) with Phe-OMe, followed by saponification of the methyl ester with 1N NaOH(aq)/dioxane. This final coupling gives the completely protected linear heptapeptide Pmp(S-Acm)-D-Tyr(Et)-Phe-Val-Asn-Cys(S-Acm)Pro-A.

The heptapeptide or hexapeptide of formula IV is, then, oxidatively cyclized using iodine in methanol to yield, after evaporation, the crude cyclic peptide whose terminal amino protecting group is removed by treatment with anhydrous hydrogen fluoride. Final purification is accomplished by countercurrent distribution and by chromatography through G-15 to give end products such as those exemplified above.

EXAMPLE 13

Substituting the appropriate protected amino acids in the above synthetic sequences gives the respective cysteine or proline acids, the basic peptide end products or a salt thereof as follows:

a. [1-($\beta$-mercapto-$\beta$,$\beta$-cyclopentamethylenepropionic acid)2-(O-ethyl-D-tyrosine)-3-(4'-methyl-phenylalanine)-7-D-proline-8-(1,5-diaminopentane)-8-desarginine-9-desglycinamide]-vasopressin b. [1-($\beta$-mercapto-$\beta$,$\beta$-cyclopentamethylenepropionic acid)-2-(O-ethyl-D-tyrosine)-4-($\alpha$-aminobutyric acid)-7-(N-methyl-alanine)-8-(1,6-diaminoheptane)-8-desarginine-9-desglycinamide]-vasopressin c. [1-($\beta$-mercapto-$\beta$,$\beta$-cyclohexamethylenepropionic acid)-2-(O-ethyl-D-tyrosine)-4-cyclohexylglycine-7-L-sarcosine-8-(1,5-diaminoheptane)-8-desarginine-9-desglycinamide]-vasopressin d. [1-($\beta$-mercapto-$\beta$,$\beta$-cyclopentamethylenepropionic acid)-4-glutamine-8-(1,5-diaminopentane)-8-desarginine-9-desglycinamide]-vasopressin e. [1-($\beta$-mercapto-$\beta$,$\beta$-cyclopentamethylenepropionic acid)-2-D-phenylalanine-4-valine-7-(1-amino-5-guanidinopentane)-7-desproline-8-desarginine-9-desglycinamide]-vasopressin f. [1-($\beta$-mercapto-$\beta$,$\beta$-cyclopentamethylenepropionic acid)-2-D-$\alpha$-aminophenylbutyric acid-4-isoleucine-7-D-proline-8-(1-amino-4-methylaminobutane)-8-desarginine-9-desglycinamide]-vasopressin g. [1-($\beta$-mercapto-$\beta$,$\beta$-cyclopentamethylenepropionic acid)-2-D-phenylalanine-4-glutamine-7-(1-methylamino-5-propylaminopentane)-7-desproline-8-desarginine-9-desglycinamide]-vasopressin.

EXAMPLE 14

Parenteral Dosage Unit Compositions

A preparation which contains 0.10 mg of the heptapeptide of Examples 3, 4 or 5 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophylized. The powder is reconstituted before either intramuscular or intervenous injection to a subject suffering from edema susceptible to anti-ADH mechanism of action. The injection is repeated as necessary, from 1-5 times daily, or in continuous i.v. drip injection.

Nasal Dosage Unit Compositions

25 Mg of finely ground heptapeptide of this invention, such as the product of Example 4, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to an edematous subject from 1-6 times a day.

What is claimed is:

1. A polypeptide compound having the formula:

$$\begin{array}{c} CH_2-CH_2 \\ / \quad \backslash \\ (CH_2)_m \quad C \\ \backslash \quad / \\ CH_2-CH_2 \end{array} \begin{array}{c} CH_2CO-X-Z-Y-Asn-Cys-P-A \\ | \\ | \\ S————————S \end{array}$$

in which:

A is $$-NR-(CH_2)_n-NR_2 \text{ or } -NR-(CH_2)_n-NH-\overset{NH}{\overset{\|}{C}}-NR_2;$$

Z is Phe, Phe(4'-Alk) or Tyr(Alk);

X is D-Phe, D-Phe(4'-Alk), D-Val, D-Nva, D-Leu, D-Ile, D-Pba, D-Nle, D-Cha, D-Abu, D-Met, D-Chg, D-Tyr, L-Tyr, D-Tyr(Alk) or L-Tyr(Alk);

P is D-Pro, L-Pro, $\Delta^3$-Pro, L-Ala, L-N-MeAla, Gly, Sar or a single bond;

Y is Val, Ile, Abu, Ala, Chg, Gln, Lys, Cha, Nle, Phe, Leu or Gly;

R is, in each case, hydrogen or $C_{1-5}$-alkyl;

n is an integer from 2-8; and m is an integer from 0-2; or a pharmaceutically acceptable, acid addition salt thereof.

2. The compound of claim 1 in which X is D-Tyr(Et).

3. The compound of claim 1 in which X is L-Tyr and Y is Gln.

4. The compound of claim 1 in which X is D-Tyr(Et); Z is Phe; Y is Val; P is Pro; m is 0 or 1 and n is 2-6.

5. The compound of claim 1 having the formula:

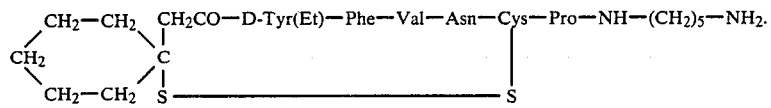

6. The compound of claim 1 having the formula:

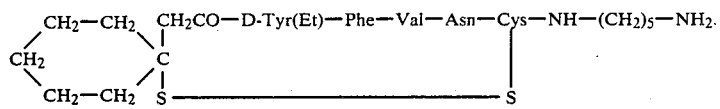

7. The compound of claim 1 having the formula:

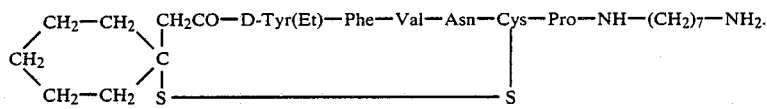

8. The compound of claim 1 having the formula:

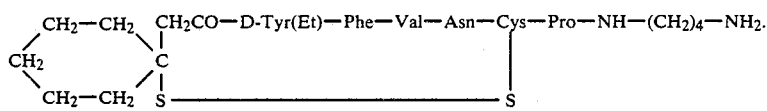

9. The compound of claim 1 having the formula:

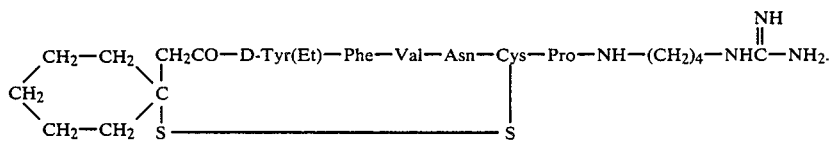

10. A pharmaceutical composition having vasopressin antagonist activity comprising a pharmaceutical carrier and, dispersed therein, an effective therefor but nontoxic quantity of a compound of claim 1.

11. The composition of claim 10 in which X is D-Tyr(Et).

12. The composition of claim 10 in which the compound has the formula:

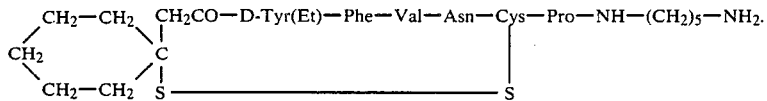

13. The composition of claim 10 in which the compound has the formula:

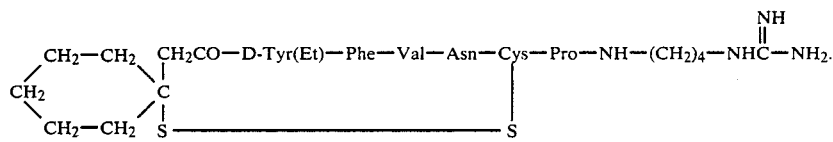

14. The composition of claim 10 in which the compound has the formula:

15. The method of inducing a vasopressin antagonist effect in a patient in need of such an effect comprising administering parenterally or intranasally to said patient a nontoxic, effective quantity therefor of a compound of claim 1.

16. The method of claim 15 in which the antagonist effect is manifested by a water diuresis.

17. The method of claim 15 in which the compound has the formula:

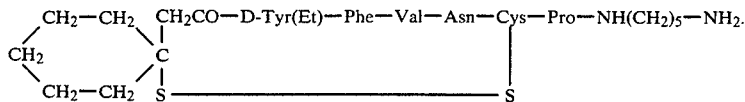

18. The method of claim 15 in which the compound has the formula:

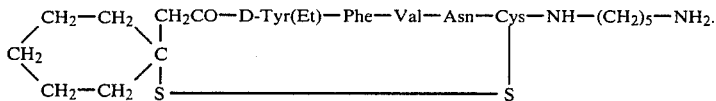

19. The method of claim 15 in which the quantity is selected from the range of 0.05–10 mg/kg administered from 1–5 times daily.

20. A polypeptide of the formula:

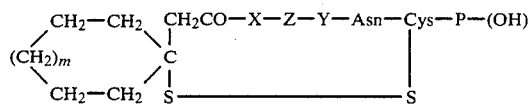

in which:

X is D-Phe, D-Phe(4'-Alk), D-Val, D-Nva, D-Leu, D-Ile, D-Pba, D-Nle, D-Cha, D-Abu, D-Met, D-Chg, D-Tyr, L-Tyr, D-Tyr(Alk) or L-Tyr(Alk);

Z is Phe, Phe(4'-Alk) or Tyr(Alk);

Y is Val, Ile, Abu, Ala, Chg, Gln, Lys, Cha, Nle, Phe, Leu or Gly;

P is D-Pro, L-Pro, $\Delta^3$-Pro, L-Ala, L-N-MeAla, Gly, Sar or a single bond; and m is a integer from 0–2; or an acceptable salt or ester thereof.

21. The compound of claim 20 being [1-($\beta$-mercapto-$\beta$,$\beta$-cyclopentamethylenepropionic acid)-2-(O-ethyl-D-tyrosine)-4-valine-8-desarginine-9-desglycinamide]-vasopressin.

22. The compound of claim 20 being [1-($\beta$-mercapto-$\beta$,$\beta$-cyclopentamethylenepropionic acid)-2-D-tyrosine-4-valine-8-desarginine-9-desglycinamide]-vasopressin.

23. The compound of claim 20 being [1-($\beta$-mercapto-$\beta$,$\beta$-cyclopentamethylenepropionic acid)-2-(O-ethyl-D-tyrosine)-4-valine-7-desproline-8-desarginine-9-desglycinamide]-vasopressin.

* * * * *